US007251869B1

(12) United States Patent
Brown, Sr. et al.

(10) Patent No.: US 7,251,869 B1
(45) Date of Patent: Aug. 7, 2007

(54) BURIAL DEVICE

(76) Inventors: Vince Brown, Sr., 1704 W. Lehigh Ave., Philadelphia, PA (US) 19132; Mardine D. Brown, Sr., 1704 W. Lehigh Ave., Philadelphia, PA (US) 19132

( * ) Notice: Subject to any disclaimer, the term of this patent is extended or adjusted under 35 U.S.C. 154(b) by 0 days.

(21) Appl. No.: 11/561,918

(22) Filed: Nov. 21, 2006

(51) Int. Cl.
*A61F 17/60* (2006.01)

(52) U.S. Cl. ............................................. 27/2; 52/136

(58) Field of Classification Search ...................... 27/2, 27/4, 35; 52/128, 136; D99/1, 2, 9
See application file for complete search history.

(56) References Cited

U.S. PATENT DOCUMENTS 2,179,409 A * 11/1939 Hulsart ....................... 362/154
2,822,685 A * 2/1958 Wesley et al. ................ 52/137
2,882,584 A * 4/1959 Kidd ............................ 27/11
2,913,895 A * 11/1959 Blasius et al. ................ 52/137
3,230,674 A * 1/1966 Christensen ............... 52/127.1
3,997,949 A 12/1976 Waltz
4,237,590 A * 12/1980 Work ............................ 27/35
4,324,026 A * 4/1982 Craft ............................... 27/1
4,962,574 A 10/1990 Estes
5,161,288 A 11/1992 Chatman
5,426,573 A * 6/1995 Jenkins ....................... 362/154
5,548,880 A 8/1996 Harb
5,590,446 A * 1/1997 Hicks .............................. 27/1
5,704,103 A * 1/1998 Crowley et al. ................. 27/1
5,746,030 A * 5/1998 Sannipoli, Sr. .............. 52/136
5,797,499 A * 8/1998 Pinco ........................ 211/13.1
6,318,030 B1 * 11/2001 McClure et al. .............. 52/136
6,324,793 B1 * 12/2001 Klanke ...................... 52/124.2
6,898,830 B1 * 5/2005 Acton et al. ..................... 27/2
6,976,294 B2 12/2005 Biondo et al.

* cited by examiner

*Primary Examiner*—William L. Miller

(57) ABSTRACT

A burial device that resembles a coffin and has an extra compartment that allows two bodies to be buried at the same time and in the same grave. The burial device essentially allows two family members or acquaintances to be buried in the same grave at the same time. The burial device is most appropriate for when the two family members or acquaintances pass away at the same time and would ensure that they would be separated, even in death. Furthermore, the burial device saves on cost and resources by having only one coffin.

10 Claims, 5 Drawing Sheets

FIG. 1
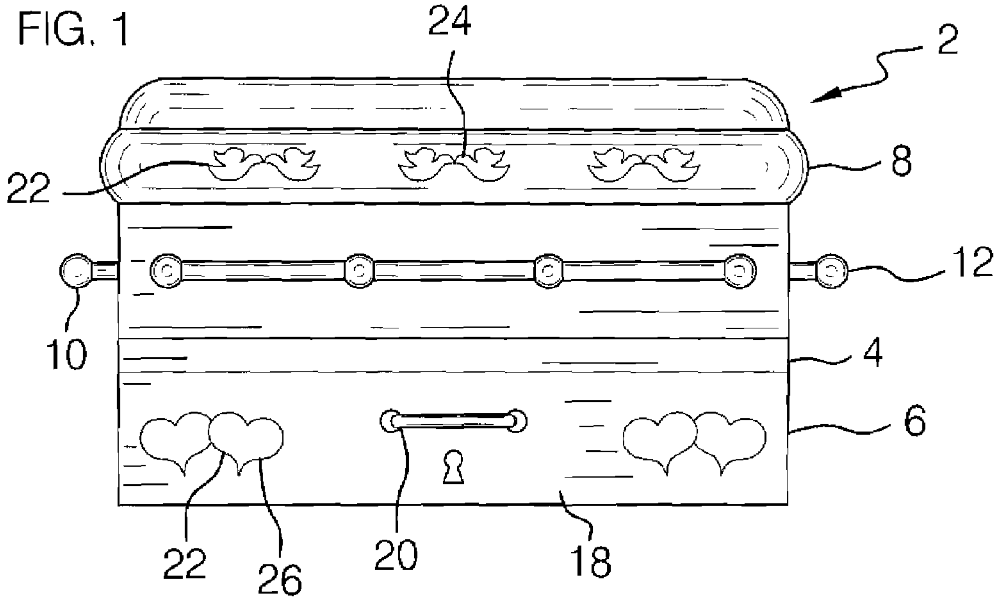
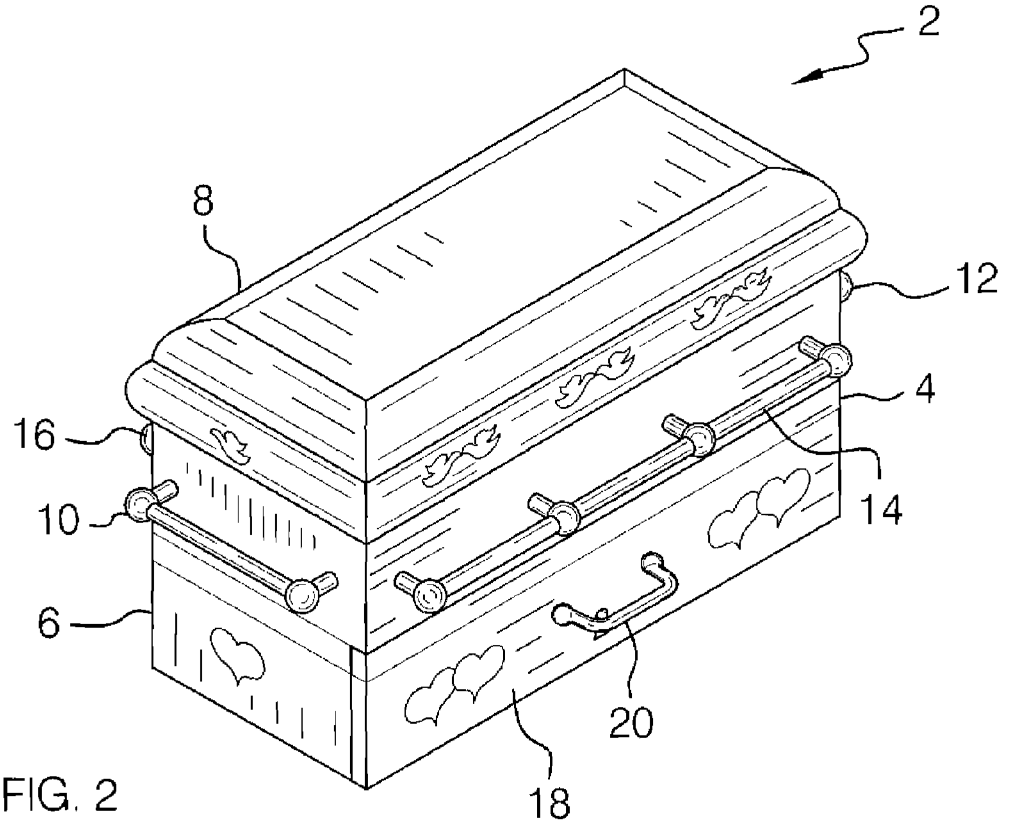
FIG. 2

BURIAL DEVICE

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

The present invention concerns that of a new and improved burial device that resembles a coffin and also has an extra compartment that allows two bodies to be buried at the same time and in the same grave.

DESCRIPTION OF THE PRIOR ART

U.S. Pat. No. 5,548,880, issued to Harb, discloses a burial compartment for two bodies which comprises an outer container and two inner containers separated by two inner panels and a center panel.

U.S. Pat. No. 5,161,288, issued to Chatman, discloses a casket construction that includes a central container cavity.

U.S. Pat. No. 4,962,574, issued to Estes, discloses a plural display casket that utilizes two substantially equal top portions which are hingedly attached to opposed sides of a casket body.

U.S. Pat. No. 3,997,949, issued to Waltz, disclosed a burial vault that is dimensioned to accommodate two caskets side-by-side and both the chambers and the covers therefore include lengthwise sections.

U.S. Pat. No. 6,976,294, issued to Biondo et al., discloses a casket that has an integral memorabilia compartment for the placement, display and storage therein of personal effects and mementos of memorialization of the deceased.

SUMMARY OF THE INVENTION

The present invention concerns that of a new and improved burial device that resembles a coffin and has an extra compartment that allows two bodies to be buried at the same time and in the same grave. The burial device essentially allows two family members or acquaintances to be buried in the same grave at the same time. The burial device is most appropriate for when the two family members or acquaintances pass away at the same time and would ensure that they would be separated, even in death. Furthermore, the burial device saves on cost and resources by having only one coffin.

There has thus been outlined, rather broadly, the more important features of a burial device that the detailed description thereof that follows may be better understood and in order that the present contribution to the art may be better appreciated. There are, of course, additional features of the burial device that will be described hereinafter and which will form the subject matter of the claims appended hereto.

In this respect, before explaining at least one embodiment of the burial device in detail, it is to be understood that the burial device is not limited in its application to the details of construction and to the arrangements of the components set forth in the following description or illustrated in the drawings. The burial device is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present burial device. It is important, therefore, that the claims be regarded as including such equivalent constructions insofar as they do not depart from the spirit and scope of the present invention.

It is therefore an object of the present invention to provide a burial device which has all of the advantages of the prior art and none of the disadvantages.

It is another object of the present invention to provide a burial device which may be easily and efficiently manufactured and marketed.

It is another object of the present invention to provide a burial device which is of durable and reliable construction.

It is yet another object of the present invention to provide a burial device which is economically affordable and available for relevant market segment of the purchasing public.

Other objects, features and advantages of the present invention will become more readily apparent from the following detailed description of the preferred embodiment when considered with the attached drawings and appended claims.

BRIEF DESCRIPTION OF THE DRAWINGS

FIG. 1 shows a front view of the burial device as it would appear in use with the lid closed.

FIG. 2 shows a perspective view of the burial device as it would appear in use with the lid closed.

DESCRIPTION OF THE PREFERRED EMBODIMENT

Figure 3:
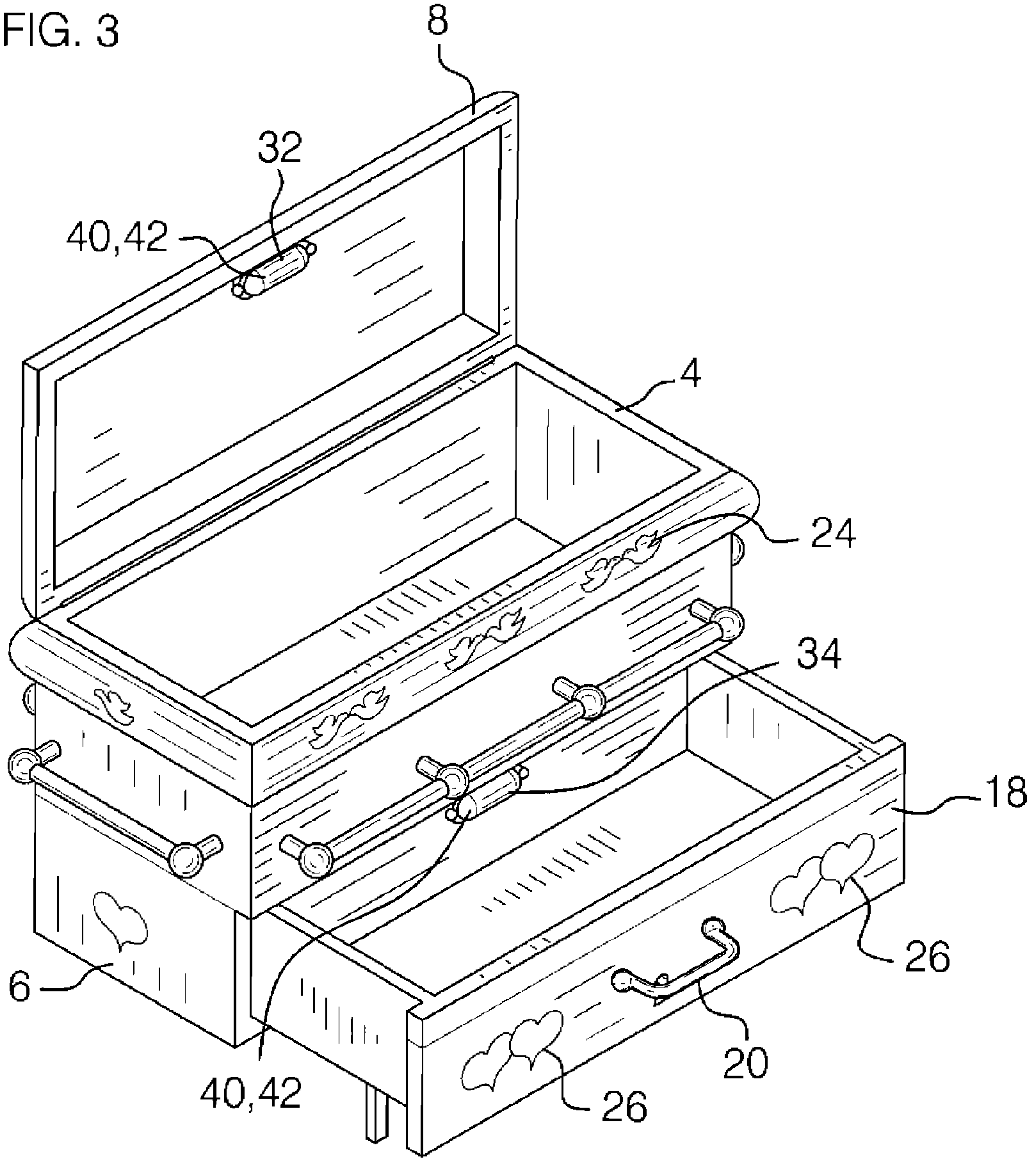
FIG. 3 shows a top perspective view of the burial device as it would appear in use, with the lid and drawer both open.
Figure 4:
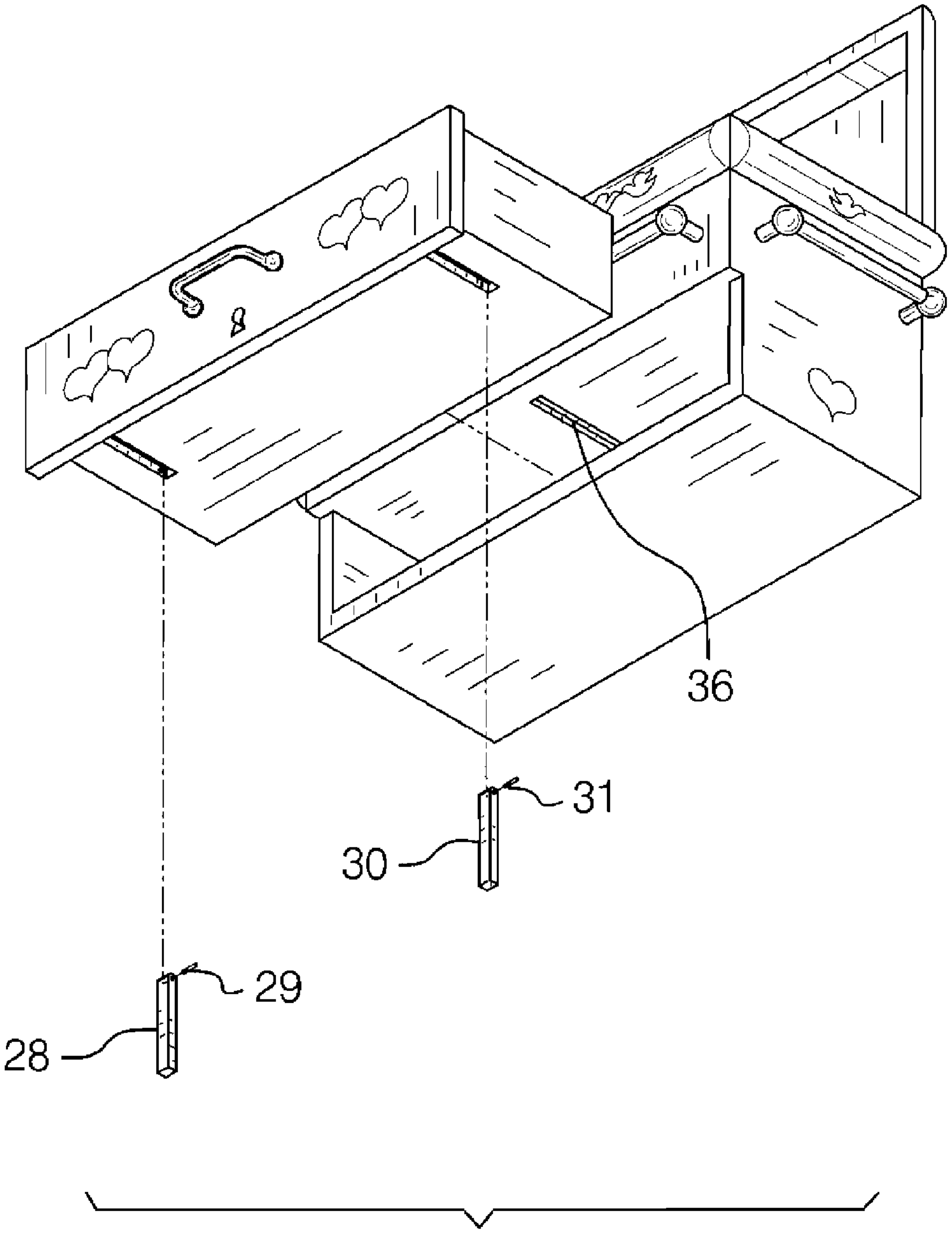
FIG. 4 shows a bottom perspective view of the burial device as it would appear in use, with the lid and drawer both open, and also highlighting the pivotable legs attached to the bottom of the drawer.
Figure 5:
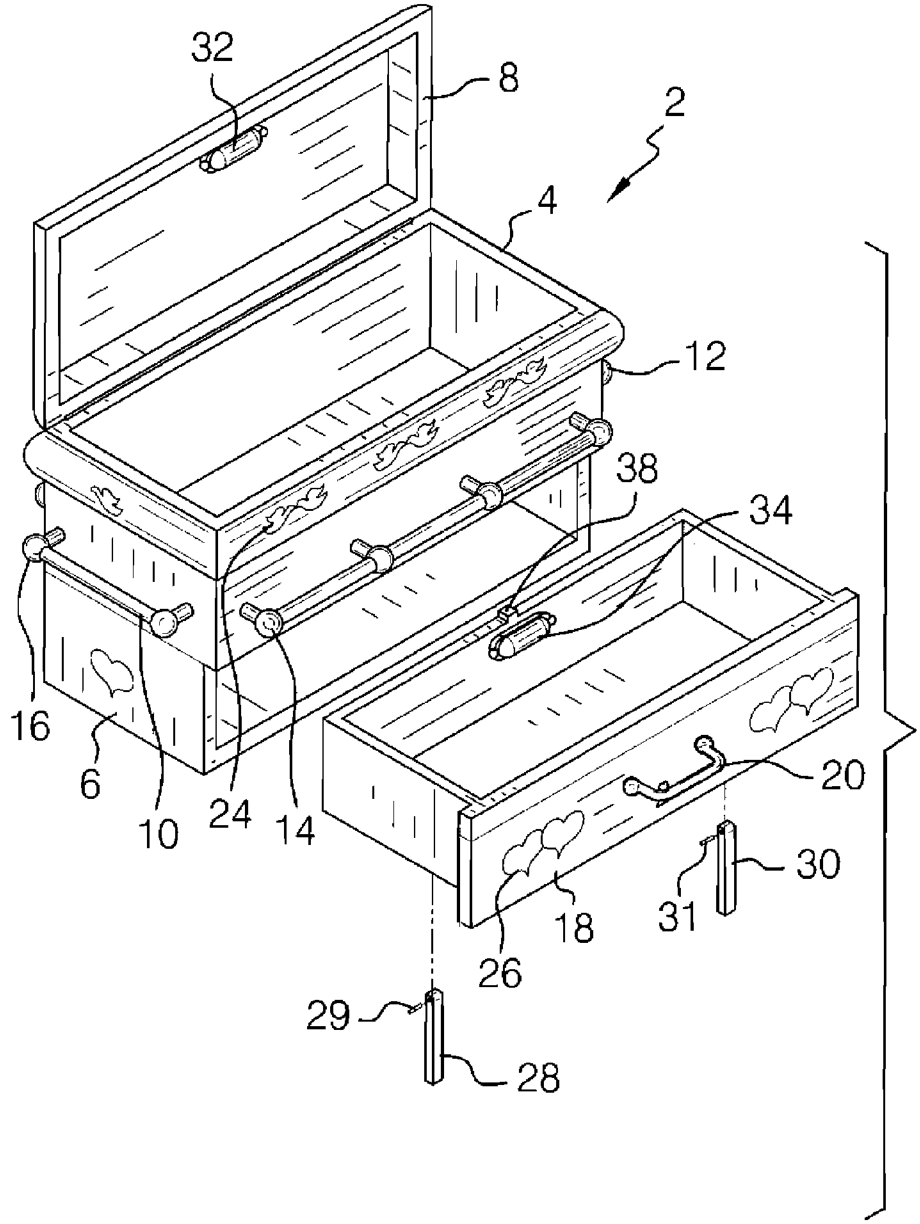
FIG. 5 shows a top perspective view of the burial device as it would appear in use, with the lid and drawer both open, and also highlighting the pivotable legs attached to the bottom of the drawer.
Figure 6:
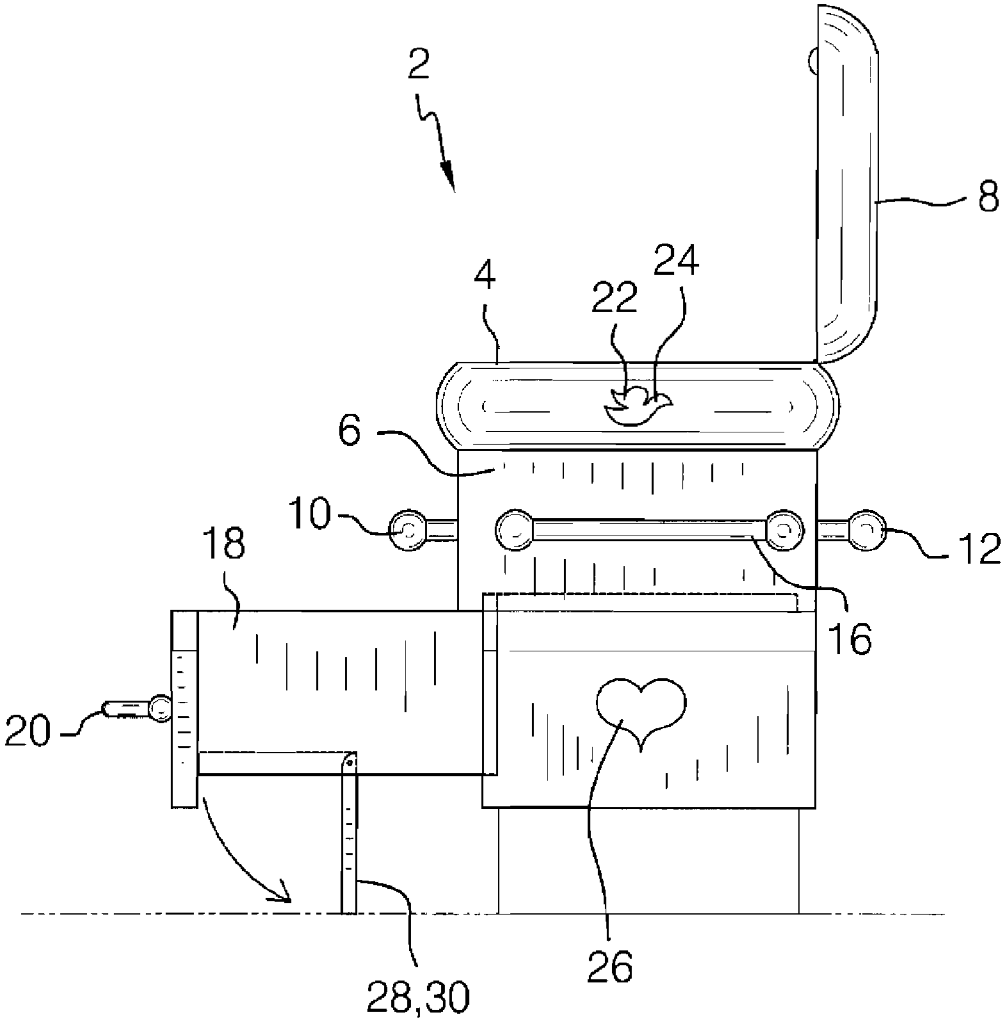
FIG. 6 shows an end view of the burial device as it would appear in use, with the lid and drawer both open, and also highlighting the pivotable legs attached to the bottom of the drawer.

With reference now to the drawings, and in particular to FIGS. 1 through 6 thereof, a new burial device embodying the principles and concepts of the present invention and generally designated by the reference numeral 2 will be described.

As best illustrated in FIGS. 1 through 6, the adjustable temperature burial device 2 comprises a coffin 4 that has two ends comprising a first end and a second end, and furthermore, has two sides comprising a first side and a second side. The coffin 4 itself comprises a base 6 and a lid 8 pivotally attached to the base 6.

The coffin 4 has a plurality of pall bearer handles that allow the coffin 4 to be effectively carried when in use. The coffin 4 includes a front handle 10 attached to the first end of the coffin 4 and a rear handle 12 attached to the second end of the coffin 4. In addition, the coffin includes first side handle 14 attached to the first side of the coffin 4 and a second side handle 16 attached to the second side of the coffin 4.

The burial device 2 has a somewhat greater height than a typical coffin 4. This height is due to the presence of drawer 18, which pulls out from the base 6 and has enough height to allow placement of a human body within it. The drawer 18 can be opened and closed with lower handle 20 and once fully pulled out, can be supported by legs 28 and 30, which are pivotally attached to drawer 18. Legs 28 and 30 are connected to the coffin 4 through the use of pins 29 and 31, respectively.

The coffin 4 also preferably includes at least two lights 32 and 34 to assist viewing bodies when coffin 4 is in use. Upper light 32 is designed to be mounted on an inner cover of the lid 8, while lower light 34 is designed to be mounted within the drawer 18 so that a body within the drawer 18 can be easily viewed when the drawer is opened. Lights 32 and 34 are preferably powered by at least one battery 40 each that are located in attached battery compartments 42.

The drawer 18 is loosely mounted in groove 36 within the coffin 4 through the presence of a drawer stop 38 that is attached to the drawer 18. When the drawer 18 is pulled out almost to the point where the drawer is just about completely removed from the coffin 4, the drawer stop 38 will reach the end of the groove 36, and at this time, the drawer 18 can not be pulled out anymore beyond this point. The interaction of groove 36 and drawer stop 38 also acts to prevent the drawer 18 from being pulled completely out, which would be potentially embarrassing if the coffin 4 were in use and a body were located within the drawer 18.

The coffin 4 further includes a plurality of designs 22 on its exterior. While these designs could clearly be any one of a number of items, they should something that is religious, peaceful, or otherwise somehow pleasing or comforting. Therefore, some preferred designs that are used with the coffin 4 of the burial device 2 are designs of doves 24 and hearts 26. Use of these two designs can be mixed and intermixed any which way on the coffin 4.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What we claim as our invention is:

1. A burial device adapted to contain a first deceased and a second deceased, the burial device comprising:

(a) a coffin having two ends comprising a first end and a second end, the coffin also having two sides comprising a first side and a second side, the coffin defining a first storage area for containing the first deceased, (b) a lid pivotally attached to the coffin, (c) means for lifting the burial device, (d) a base integral to the coffin and positioned below the first storage area, (e) a secondary storage area located within the base for containing the second deceased, (f) means for partially retracting the secondary storage area out of the base, (f) means for lighting the coffin and the base, and (h) means for preventing the secondary storage area from being completely pulled out of the base.

2. A burial device according to claim 1 wherein the means for lifting the burial device comprises:

(a) a pair of end handles comprising a front handle and a rear handle, the front handle being attached to the first end of the coffin, the rear handle being attached to the second end of the coffin, (b) a pair of side handles comprising a first side handle and a second side handle, the first side handle being attached to the first side of the coffin, the second side handle being attached to the second side of the coffin.

3. A burial device according to claim 2 wherein the secondary storage area located within the base comprises a drawer.

4. A burial device according to claim 3 wherein the means for partially retracting the secondary storage area out of the base comprises:

(a) a drawer handle attached to the drawer.

5. A burial device according to claim 4 wherein the means for lighting the coffin and the base comprises (a) a first light attached to the lid, (b) a second light attached to the base within the drawer of the base, and (c) power means to provide power to each light.

6. A burial device according to claim 5 wherein the power means to provide power to each light comprises:

(a) a battery compartment located within each light, and (b) at least one battery located within each battery compartment.

7. A burial device according to claim 6 wherein the means for preventing the secondary storage area from being completely pulled out of the burial device comprises:

(a) a drawer stop located within the base, (b) a groove located on the drawer, (c) wherein pulling out the drawer almost completely from the base allows the groove to connect with the drawer stop, thereby preventing the drawer from being further pulled out.

8. A burial device according to claim 7 wherein the burial device further comprises a plurality of included designs.

9. A burial device according to claim 8 wherein the plurality of included designs comprises at least one heart.

10. A burial device according to claim 8 wherein the plurality of included designs comprises at least one dove.

* * * * *